(12) United States Patent
Weisshaupt et al.

(10) Patent No.: US 11,141,211 B2
(45) Date of Patent: *Oct. 12, 2021

(54) ANASTOMOSIS DEVICE WITH COLLAPSIBLE DISTAL HEAD ELEMENT

(71) Applicant: Aesculap AG, Tuttlingen (DE)

(72) Inventors: Dieter Weisshaupt, Immendingen (DE); Christoph Rothweiler, Donaueschingen (DE)

(73) Assignee: AESCULAP AG, Tuttlingen (DE)

( * ) Notice: Subject to any disclaimer, the term of this patent is extended or adjusted under 35 U.S.C. 154(b) by 1032 days.

This patent is subject to a terminal disclaimer.

(21) Appl. No.: 15/784,634

(22) Filed: Oct. 16, 2017

(65) Prior Publication Data

US 2018/0036063 A1 Feb. 8, 2018

Related U.S. Application Data

(63) Continuation of application No. 14/356,250, filed as application No. PCT/EP2012/071941 on Nov. 6, 2012, now Pat. No. 9,820,804.

(30) Foreign Application Priority Data

Nov. 10, 2011 (DE) .................... 10 2011 055 236.7

(51) Int. Cl.
*A61B 18/14* (2006.01)
*A61B 17/115* (2006.01)
(Continued)

(52) U.S. Cl.
CPC .......... *A61B 18/14* (2013.01); *A61B 17/1155* (2013.01); *A61B 17/00234* (2013.01);
(Continued)

(58) Field of Classification Search
None
See application file for complete search history.

(56) References Cited

U.S. PATENT DOCUMENTS 4,700,703 A 10/1987 Resnick et al.
4,893,622 A 1/1990 Green et al.
(Continued)

FOREIGN PATENT DOCUMENTS

DE 202010013152 U1 3/2011
DE 102009059196 A1 6/2011

OTHER PUBLICATIONS

Chinese Office Action for Chinese Application No. 201280055245.3, dated Dec. 16, 2016 with translation—16 Pages.
(Continued)

*Primary Examiner* — Luther Behringer

(57) ABSTRACT

A surgical instrument for bonding body tissue includes an instrument shank or shaft, a first tool element, a second tool element axially movable relative to the first tool element, and an annular sleeve-like cutting element. The second tool element includes a plurality of tool element members that are radially deflectable. The first and second tool elements are each equipped with at least one electrode. The second tool element includes a biasing member that biases the tool element members in a radially inward direction. A stop member is operable in a first position to hold the tool element members against the biasing force of the biasing member in which the tool element members assume a maximum outer diameter. The stop member is further operable in a second position to release the tool element members such that the tool element members can deflect radially inwardly and cut body tissue.

6 Claims, 15 Drawing Sheets

(51) Int. Cl.
*A61B 17/00* (2006.01)
*A61B 17/11* (2006.01)
*A61B 18/00* (2006.01)

(52) U.S. Cl.
CPC . *A61B 17/1114* (2013.01); *A61B 2017/00862* (2013.01); *A61B 2017/111* (2013.01); *A61B 2017/1107* (2013.01); *A61B 2017/1132* (2013.01); *A61B 2017/1135* (2013.01); *A61B 2017/1139* (2013.01); *A61B 2018/0063* (2013.01); *A61B 2018/00404* (2013.01); *A61B 2018/00601* (2013.01); *A61B 2018/00607* (2013.01); *A61B 2018/1407* (2013.01); *A61B 2018/1497* (2013.01)

(56) References Cited

U.S. PATENT DOCUMENTS

| | | | |
|---|---|---|---|
| 6,699,245 | B2 | 3/2004 | Dinger et al. |
| 7,168,604 | B2 | 1/2007 | Milliman et al. |
| 9,820,804 | B2 * | 11/2017 | Weisshaupt ........ A61B 17/1155 |
| 2002/0025243 | A1 | 2/2002 | Heck |
| 2006/0111704 | A1 | 3/2006 | Brenneman et al. |
| 2011/0152861 | A1 | 6/2011 | Weisshaupt et al. |
| 2014/0309634 | A1 * | 10/2014 | Weisshaupt ........ A61B 17/1155 606/49 |

OTHER PUBLICATIONS

German Search Report for German Application No. 10 2011 055 236.7, with partial English translation, dated Jul. 18, 2012—6 pages.
International Search Report for International Application No. PCT/EP2012/071941, dated Feb. 7, 2013—11 Pages.
Non Final Office Action for U.S. Appl. No. 14/356,250, dated Feb. 12, 2016, 12 pages.
Non Final Office Action for U.S. Appl. No. 14/356,250, dated Oct. 7, 2016, 12 pages.
Final Office Action for U.S. Appl. No. 14/356,250, dated Jun. 16, 2016, 15 pages.
Final Office Action for U.S. Appl. No. 14/356,250, dated Jan. 26, 2017, 14 pages.
Notice of Allowance for U.S. Appl. No. 14/356,250, dated Jul. 19, 2017, 15 pages.
Entire patent prosecution history of U.S. Appl. No. 14/356,250, filed May 5, 2014, entitled, "Anastomosis Device With Collapsible Distal Head Element."

* cited by examiner

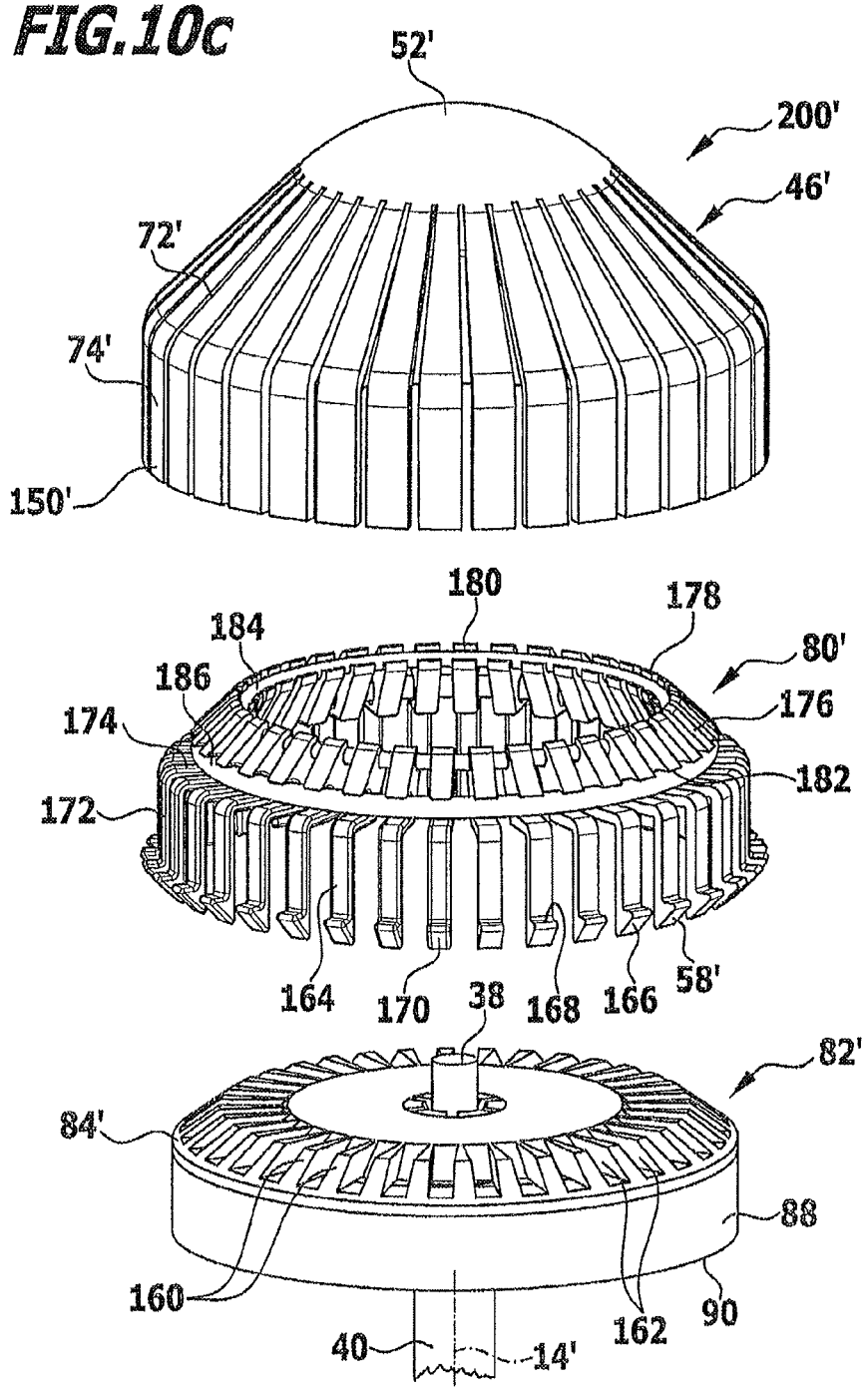

ANASTOMOSIS DEVICE WITH COLLAPSIBLE DISTAL HEAD ELEMENT

RELATED APPLICATIONS

This application is a continuation of U.S. application Ser. No. 14/356,250, filed May 5, 2014, now issued as U.S. Pat. No. 9,820,804, which is the U.S. National Phase entry of International Application No. PCT/EP2012/071941, filed Nov. 6, 2012, which claims the benefit of priority of German Application No. DE 10 2011 055 236.7, filed Nov. 10, 2011. The contents of U.S. application Ser. No. 14/356,250, International Application No. PCT/EP2012/071941, and German Application No. DE 10 2011 055 236.7 are incorporated by reference herein in their entireties.

FIELD

The present invention relates to a surgical instrument for bonding body tissue. The instrument includes a shank and first and second tool elements. The first and second tool elements are arranged or configured to be movable relative to each other. Each of the first and second tool elements includes an electrode. The electrodes define in an approximating position of the tool elements a minimum distance from each other, are opposed to each other and face each other. The first tool element is arranged or formed at the distal end of the shank.

BACKGROUND

Surgical instruments of the type described in the beginning are known from DE 20 2010 013 152 U1, for example. By said instruments hollow organs, for example vessels or intestinal portions, can be bonded in a gentle manner and without using clips or sewing material. Especially end-to-end, side-to-end and side-to-side anastomoses can be carried out.

It is a problem of said instruments to remove the same, especially the second tool elements thereof, again after bonding two body tissue parts without overstretching an anastomosis between the two body tissue parts produced by the instrument, which would endanger the operation result.

SUMMARY

Therefore it is an object of the present invention to improve a surgical instrument of the type described in the beginning so that a mechanical load of anastomoses of body tissue parts produced by means of current flow is minimized during removing the surgical instrument.

This object is achieved according to the invention in a surgical instrument of the type described in the beginning. The second tool element is adapted to be brought from an operating position, in which it can be brought into the approximating position, into a removing position. In the removing position, a peripheral withdrawing line defined by the electrode of the second tool element is shorter than a peripheral approximating line defined by the electrode in the approximating position.

The proposed further development of a surgical instrument of the type described in the beginning especially enables a length of the peripheral line defined by the electrode in the approximating position to be varied. That is, the proposed further development allows the peripheral line defined by the electrode in the approximating position to be reduced during transition into the removing position. This in particular allows varying the second tool element as to its outer appearance, especially its size, equally during transition from the approximating position into the removing position. With this feature, the second tool element can be withdrawn through the bonding made, namely the anastomosis, without deforming or even overstretching the anastomosis. By simply folding the second tool element, as it is known e.g. from DE 20 2010 013 152 U1, the anastomosis must at least be deformed when the instrument is withdrawn. A weak stretching cannot be completely excluded, either. By varying a length of the peripheral line of the electrode during transition from the approximating position into the removing position, the efficient surface defined by the second tool element is reduced. This occurs independently of an angular position of the 25 second tool element relative to a longitudinal axis defined especially by the shank in the area of the tool elements. Hence by the surgical instrument body tissue parts can be bonded even more gently than by known instruments.

It is favorable, especially also with a surgical instrument of the type described in the beginning, when a first peripheral tool line defined by the second tool element in the removing position is shorter than a second peripheral tool line defined by the second tool element in the operating position. By a second tool element which can vary its shape or outer contour in this way it is possible to move the second tool element through the bonding produced by the instrument without deforming or overstretching the anastomosis.

The manipulation of the instrument can be further improved especially in that the instrument comprises a retaining means for securing the second tool element in the operating position. Hence it can be especially ensured by the retaining means that the tool element cannot be transferred inadvertently from the operating position into the removing position.

It is of advantage when the retaining means and the second tool element are arranged to be movable relative to each other. For example, such relative movement of the retaining means and the second tool element can be used to transfer the tool element from the operating position into the removing position.

According to another preferred embodiment of the invention, it may be provided that the instrument comprises a folding mechanism for transferring the second tool element from the operating position into the removing position and/or vice versa. By the folding mechanism the shape and/or configuration of the second tool element optionally can be varied such that the peripheral approximating line can be reduced to the peripheral withdrawing line and/or the second peripheral tool line can be reduced to the first peripheral tool line.

The folding mechanism can be actuated especially easily when it comprises a first force transmission element for transmitting an actuating force to the retaining means for transferring the same from the operating position into the removing position and/or vice versa. Thus it is possible in an especially targeted manner by the first force transmission element to actuate or move the retaining means, for example purely mechanically, so as to transfer the same and the instrument, respectively, from the operating or approximating position into the removing position and/or vice versa.

Advantageously, the retaining means and a second force transmission element for transmitting an actuating force to the second tool element are movably arranged relative to each other to transfer the same from the operating position into the approximating position and/or vice versa. In this way it is especially possible to actuate the folding mechanism and the second tool element in a defined way and independently of each other.

The structural design of the surgical instrument is especially simple when the second force transmission element and the retaining means are configured to be movable and/or twistable and/or screwable relative to each other.

It is favorable when the retaining means and/or the first and/or second force transmission element are arranged to be movable relative to the shank. Thus, for example an operating surgeon is able to hold the instrument at the shank and to actuate in a well-directed and desired fashion optionally the retaining means or the first or second force transmission member, for example for bonding body tissue or removing the instrument from the body of a patient in a defined manner.

According to another preferred embodiment of the invention, the instrument can comprise an actuating mechanism coupled to the folding mechanism and/or the second force transmission element and/or the retaining means for actuating the folding mechanism and/or for moving the second force transmission member and/or the retaining means relative to the shank. The actuating mechanism can especially comprise one or more actuating elements or actuating members which are directly or indirectly coupled to the folding mechanism, the second force transmission element or the retaining means or interact with the same so as to actuate them preferably optionally.

Of preference, the second tool element comprises at least two tool element members coupled to the second electrode or supporting a part thereof. Preferably a plurality of tool element members is provided which can be designed especially identically. It is advantageous when the second tool element is rotationally symmetric related to a longitudinal axis defined by the same. In particular, the tool element members can be arranged or configured to be movable relative to one another, whereby an outer contour or shape of the second tool element can be easily modified.

The at least two tool element members are favorably arranged or configured to be movable in the radial direction relative to a longitudinal axis defined by the second tool element. For example, it may be favorable when free ends of the tool element members are movable toward the longitudinal axis upon transition from the operating position into the removing position.

It is advantageous when the at least two tool element members are in the form of arms protruding at least partly in the radial direction. These tool element members can be easily formed, for example, by cutting a second tool element in the form of an umbrella, a cover or a sleeve.

In order to obtain as stable an arrangement as possible, it is favorable when the at least two tool element members are arranged or fixed at the distal end of the second tool element and the free ends thereof point in the proximal or substantially proximal direction. In this way, especially the free ends of the tool element members can be equipped with electrode portions or can be coupled to an electrode pointing in the proximal direction and being adapted to interact with an electrode of the first tool element pointing in the distal direction.

The manufacture especially of the second tool element becomes particularly simple, when the at least two tool element members are separated from each other by a straight or curved slit extending in the radial or substantially radial direction. This enables the tool element members to be moved, for example, so far toward each other and especially also toward the longitudinal axis as there is a tolerance left by the provided slit. In other words, it is favorable when the slit has a finite width that permits reducing a distance between the tool element members in the circumferential direction upon transition from the operating position into the removing position.

It is of advantage when the electrode of the second tool element is in the form of an electrode ring having a variable periphery. Such electrode ring allows obtaining in a simple way that the peripheral approximating line is longer than the peripheral withdrawing line.

It may be favorable when the electrode ring is slotted in the radial direction. Especially plural slits can be provided. If only one slit is provided, especially free ends of the electrode ring can be moved toward each other or away from each other so as to vary a length of the peripheral line defined by the electrode. In the same way, this can also be obtained when the electrode ring is subdivided into an appropriate number of electrode portions by plural slits.

According to a further preferred embodiment of the invention, it can be provided that the electrode ring is hollow and defines an electrode ring passage and that in the electrode ring passage an electrode ring balancing element is movably held to connect free ends of the slotted electrode ring. The electrode ring balancing element enables a continuous annular electrode to be formed independently of a distance of free ends of the electrode ring separated from each other by a slit. This electrode can have a somewhat smaller outer diameter than the electrode ring itself especially in the area of the slit, viz. where the electrode ring balancing element projects especially from the free ends of the electrode ring. It is favorable when the electrode ring comprises plural electrode ring portions separated from each other by slits which are arranged or formed at a respective free end of a tool element member. For example, in a plurality of tool element members an appropriate number of electrode ring portions can be formed. These can especially define electrode surface areas pointing in the proximal direction so that the electrode in total comprises a plurality of electrode ring portions which are optionally spaced apart or contact respective adjacent electrode ring portions. So in particular also a peripheral line of the electrode can be reduced due to a movement of the tool element members upon transition from the operating position into the removing position in a desired manner.

In a particularly simple manner a continuous electrode ring can be formed, namely independently of whether the second tool element adopts the operating position or the removing position, when the electrode ring is self-contained and is made of elastic or expandable material. Preferably the material for forming the electrode ring is electrically conductive. It can especially contain nitinol or can be nitinol, whereby elasticities can be obtained which admit a variation of the peripheral line defined by the electrode by up to 8%.

Moreover, it may be advantageous when the second tool element comprises a biasing means for holding the second tool elements biased against the retaining means in the operating position. The biasing means, on the one hand, can improve the stability of the second tool element. On the other hand, the biasing means allows transferring the tool element automatically from the operating position into the removing position, for example during movement of the retaining means relative to the second tool element.

The structural design of the biasing means can be facilitated especially by the fact that it comprises at least one biasing member. Two or more biasing members may be provided as well.

The surgical instrument can be manufactured especially easily when the at least one biasing member is in the form of an at least partially spring-elastic element. In this case, especially leaf or coil springs are imaginable. Also elastic or spring-elastic plastic elements are especially taken into consideration to a certain extent.

The surgical instrument can be designed in a particularly simple and compact manner when at least part of the at least two tool element members comprises or forms a biasing member. Hence it is especially possible that the tool element members themselves constitute the biasing members. The second tool element can be made, for instance, of one or more plastic members. If the tool element members are in the form of plastic arms separated from each other, they exhibit certain innate elasticity. If they are spread into the operating position especially upon transition from the removing position into the operating position, for example by the retaining means, they keep the second tool element biased against the retaining means. When the latter is moved relative to the second tool element so that the tool element members are released, the latter can return to their home position and the second tool element can thus be automatically transferred from the operating position into the removing position.

In accordance with a further preferred embodiment of the invention, it may be provided that the retaining means comprises a stop acting in the radial direction away from a longitudinal axis of the second tool element. The at least two tool element members or the electrode of the second tool element can be directly or indirectly adjacent to said stop in the operating position. This stop is adapted to hold the tool element members for example in the afore-described deflected position. From the deflected position, the tool element members can be transferred into their home position, i.e. especially from the operating position into the removing position, again after being released by the stop.

The design of the retaining means is especially facilitated when it comprises an annular or substantially annular stop member which surrounds the longitudinal axis and forms or comprises the stop. The stop member hence can be configured especially in the form of a ring or sleeve portion. The ring or sleeve portion can include a stop surface facing away from the longitudinal axis in the radial direction. In this arrangement, the tool element members or free ends thereof can be directly or indirectly adjacent to the stop surface in the operating position.

It is of advantage when the stop member is held to be movable in parallel to the longitudinal axis and releases the at least two tool element members or the electrode of the second tool element upon transition from the operating position into the removing position. In particular when the tool elements are held against the stop member in the operating position, during movement of the stop member relative to the tool elements the latter can be transferred into a home position, especially the removing position, when the stop member is no longer adapted to act as stop, i.e. when it releases the tool element members.

It is favorable when the surgical instrument comprises a cutting element for severing body tissue. For example, projecting tissue can be resected in the area of an anastomosis between two body tissue parts produced by the instrument.

Preferably the cutting element is formed as an annular cutting blade surrounding the longitudinal axis. Such annular cutting blade is adapted to prepare an annular tissue anastomosis produced by the instrument in a desired way.

The cutting element can especially be designed as a mechanical cutting element having a sharpened cutting edge or as an HF cutting element.

The instrument can be designed in a particularly compact manner when the retaining means comprises or supports the cutting element. This permits in particular to move the cutting element, when the second tool element adopts the approximating position and two body tissue parts to be bonded are bonded by the electrodes of the first and second tool elements facing each other. When the cutting element is moved, especially also the retaining means can be moved so that it enables a transition of the second tool element from the operating position into the removing position. Hence this can be performed in particular in one step with transecting protruding tissue in the area of the tissue anastomosis.

In order to resect protruding tissue in the area of the anastomosis when the instrument is removed it is advantageous, when a cutting edge of the cutting element points in the proximal direction.

The manipulation of the surgical instrument can be improved in a simple manner in that the actuating mechanism includes at least one actuating member arranged or movably held at a proximal end or in a proximal end area of the instrument. Especially plural actuating members can be provided which are coupled to the second tool element and the retaining means, respectively. This optionally allows movement of the same relative to the shank of the instrument.

BRIEF DESCRIPTION OF THE DRAWING FIGURES

The following description of preferred embodiments of the invention serves for illustration in combination with the drawings, in which.

Figure 9A:
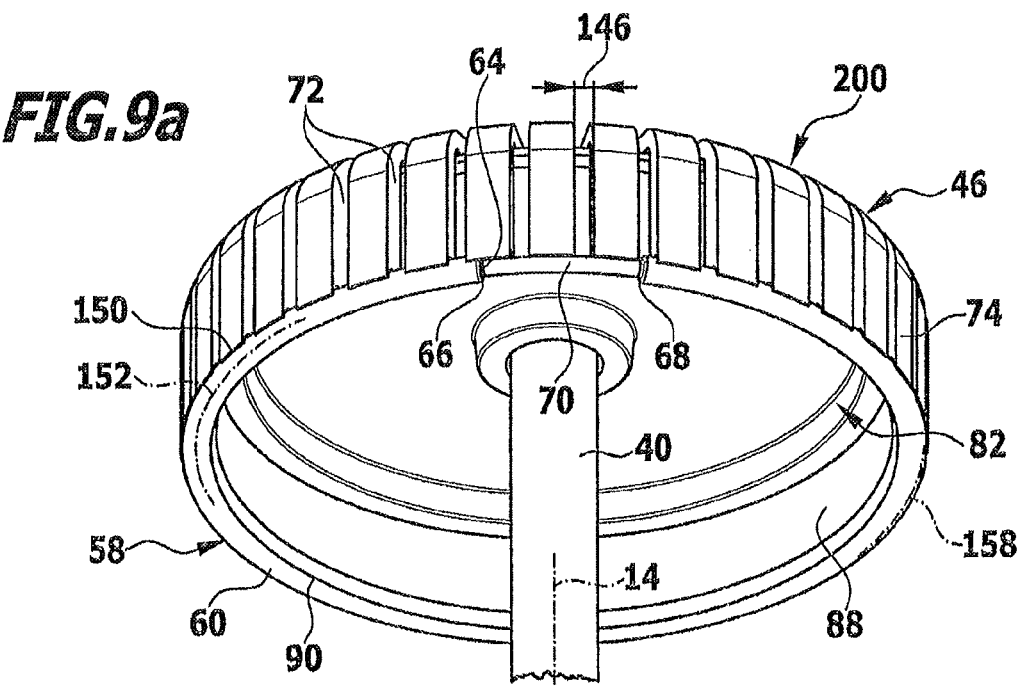
Figure 9B:
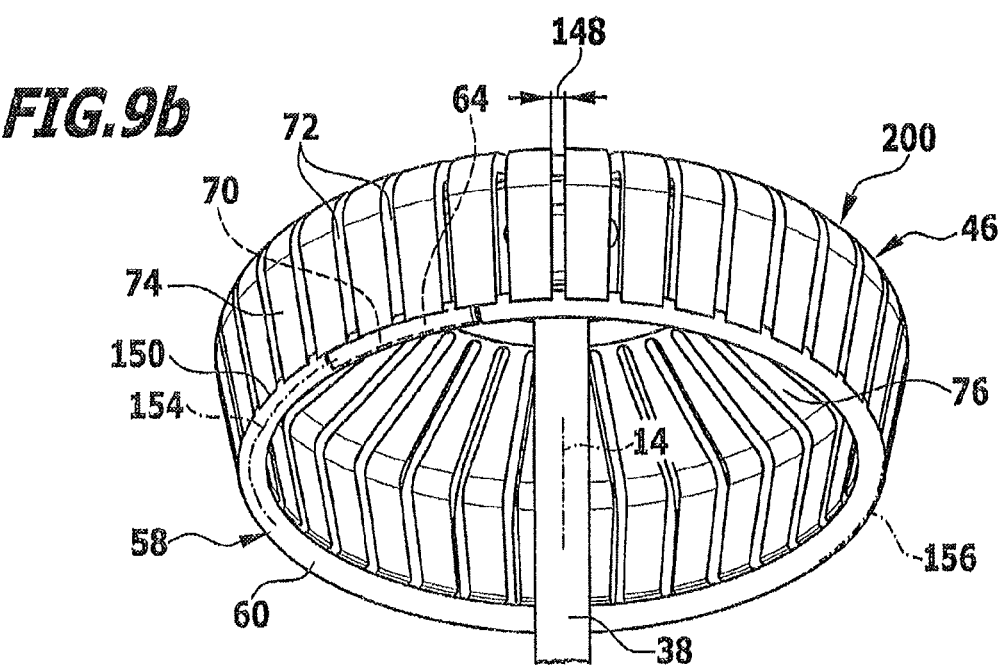
Figure 10A:
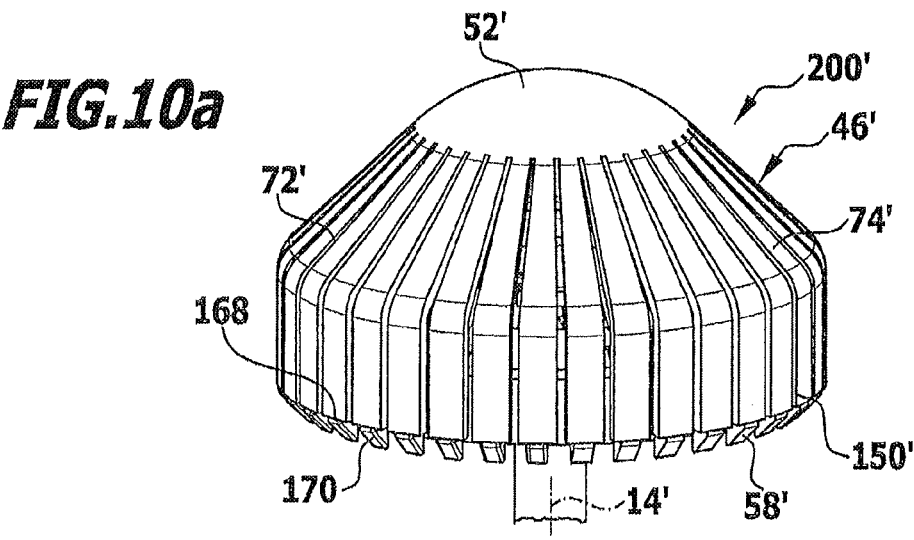
Figure 10B:
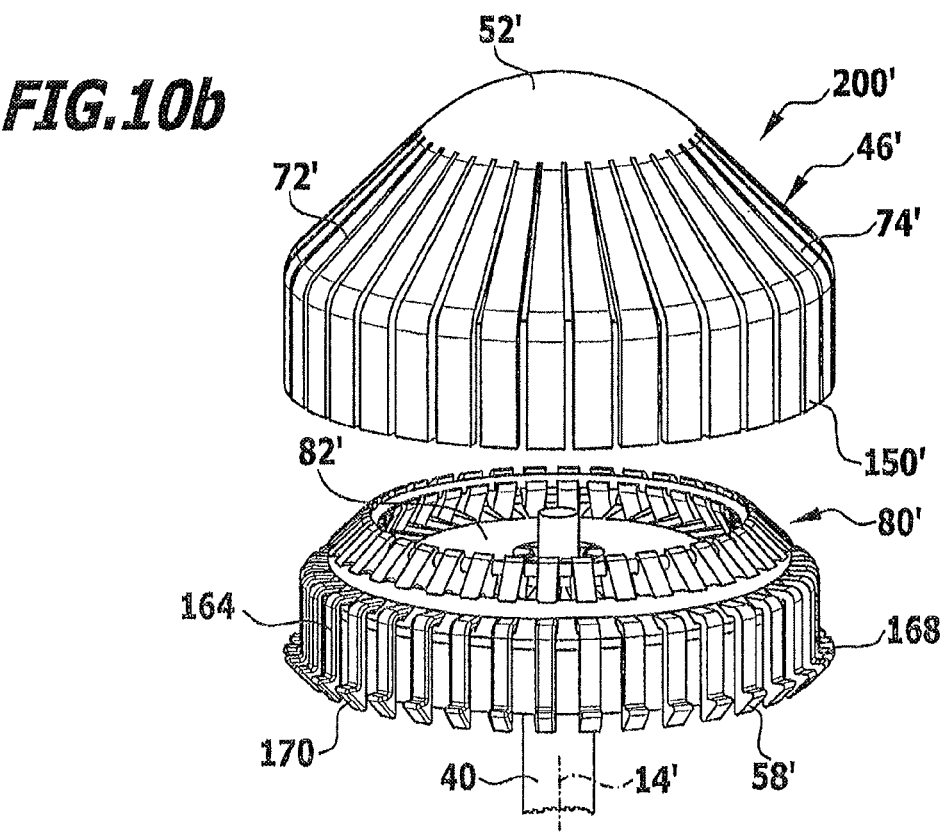
Figure 11:
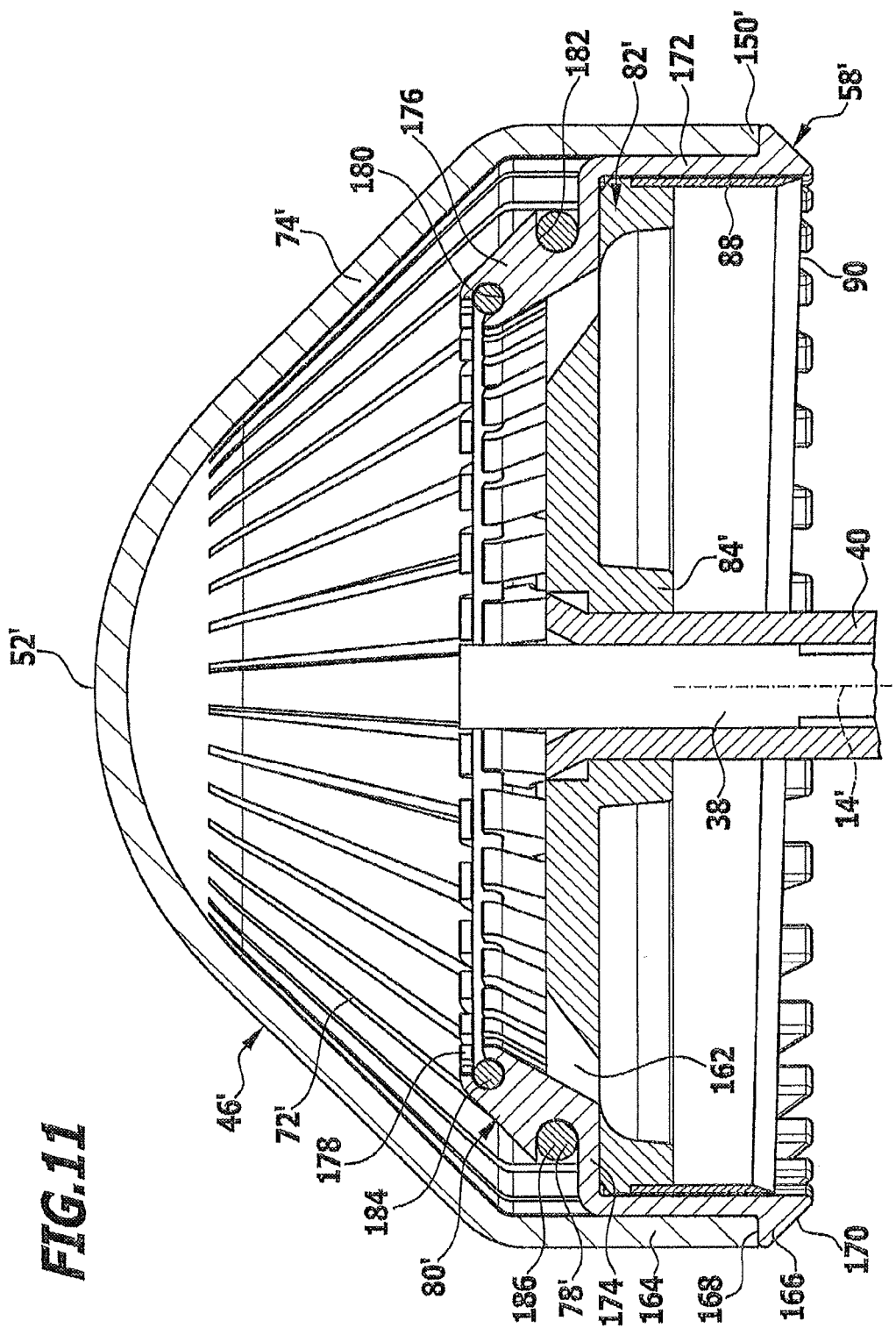
Figure 12:
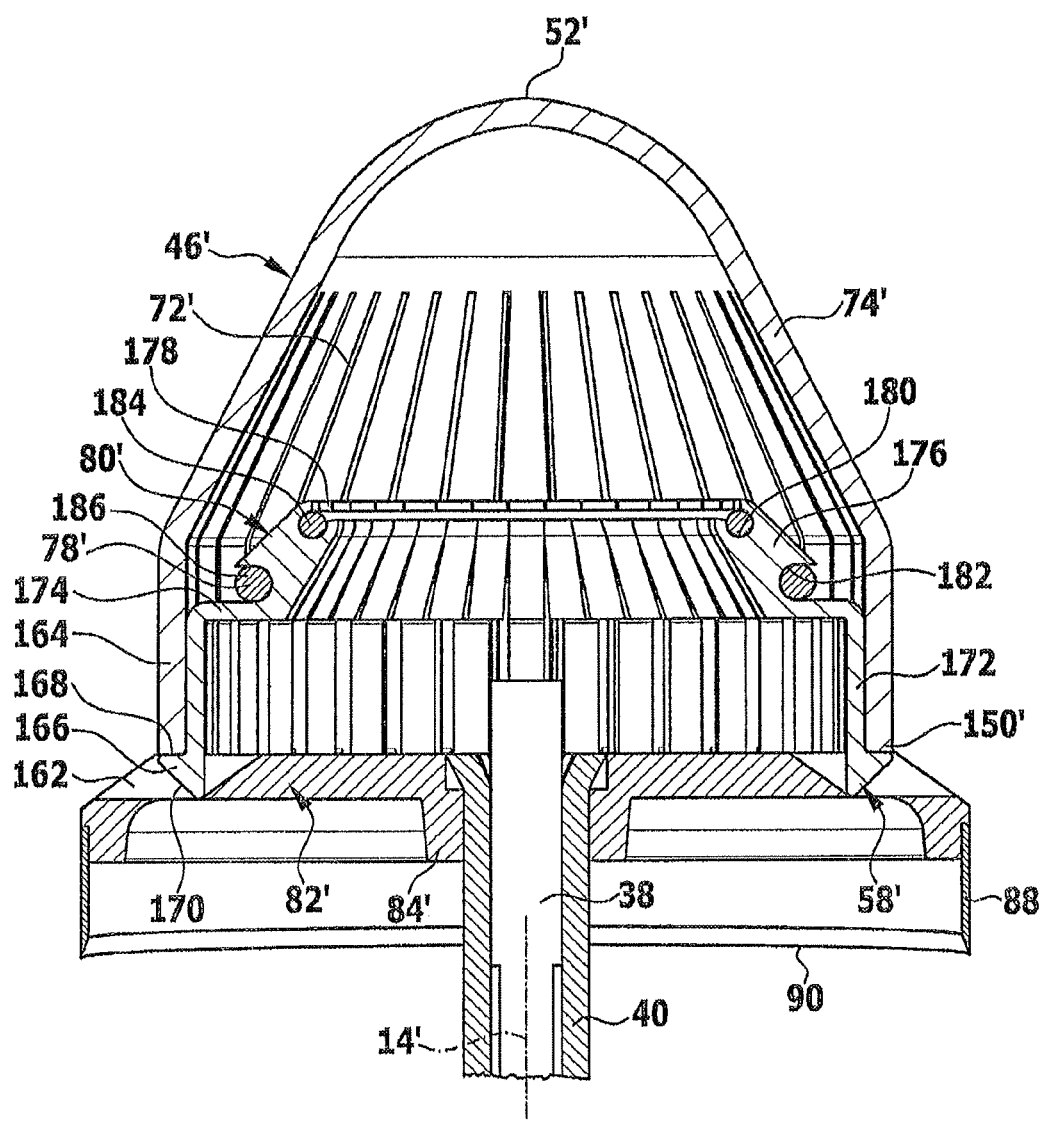
Figure 13:
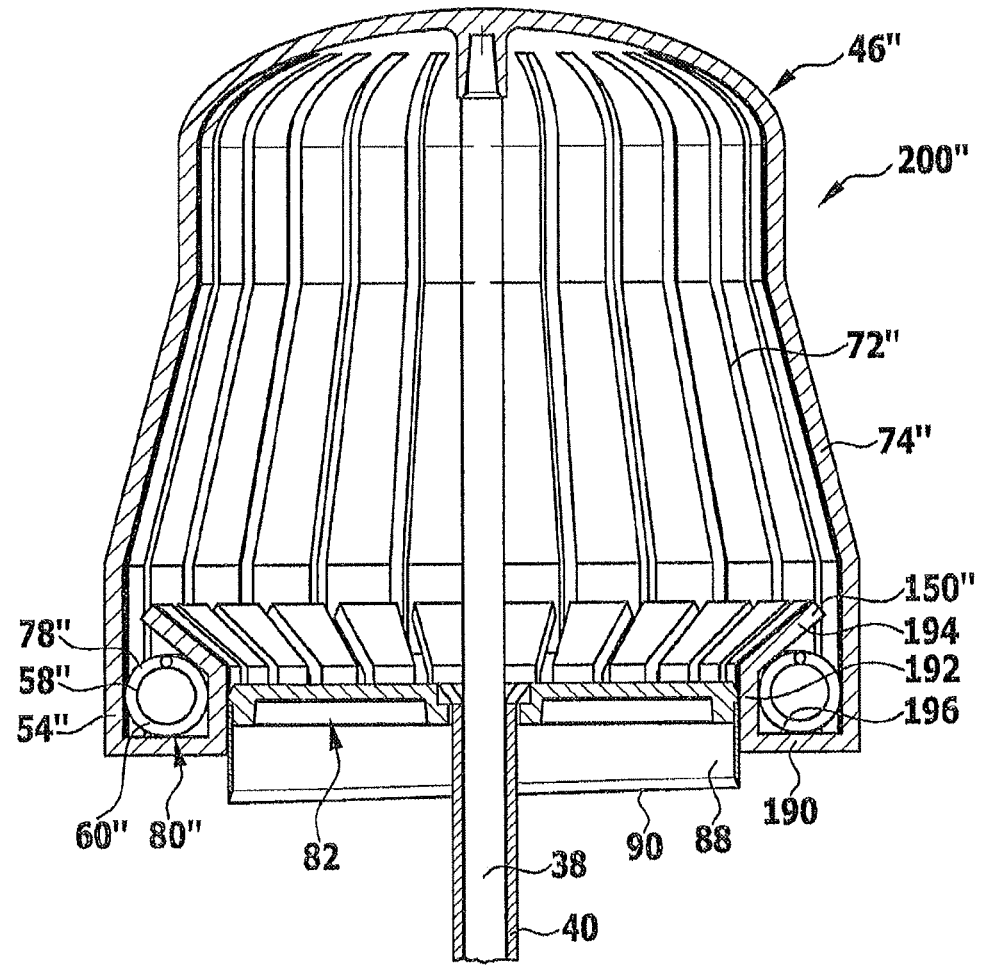
Figure 14:
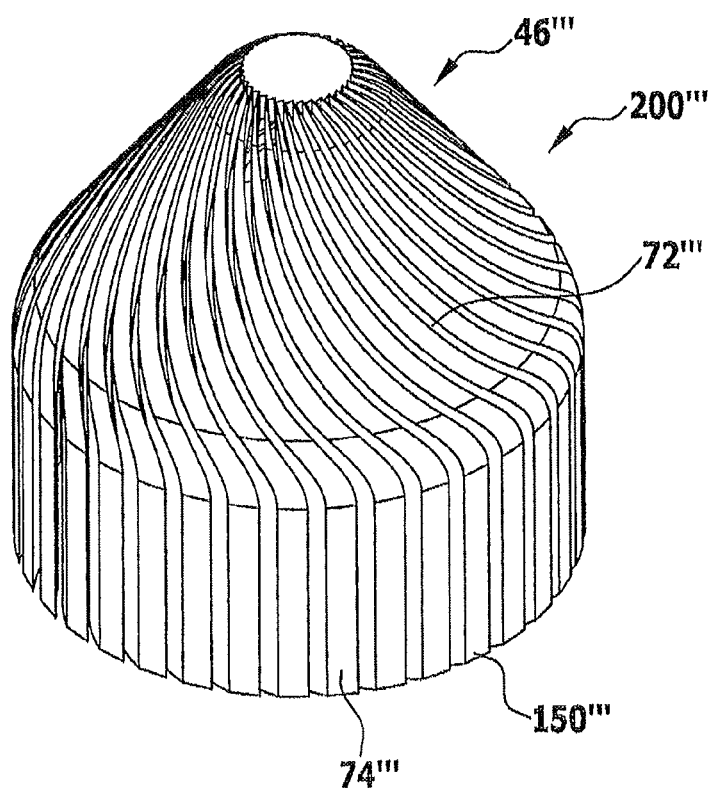

FIG. 9*a* shows a perspective view of the second tool element including the retaining means from the bottom;

FIG. 9*b* shows a view similar to the representation in FIG. 9*a* without retaining means;

FIG. 10*a* shows a perspective side view of another embodiment of a second tool element;

FIG. 10*b* is a partly exploded view of the arrangement of FIG. 10*a*;

FIG. 10*c* is an exploded view of the arrangement of FIG. 10*a*;

FIG. 11 is a longitudinal view of the second tool element shown in FIG. 10a in the operating and approximating position;

FIG. 12 is a view similar to the representation in FIG. 11, however in the removing position;

FIG. 13 is a view analogous to FIG. 11 of another embodiment of a second tool element; and FIG. 14 shows a perspective view of another embodiment of a second tool element.

DETAILED DESCRIPTION

The foregoing description thus comprises especially the embodiments of a surgical instrument which are explicitly described hereinafter:

1. A surgical instrument (10) for bonding body tissue (126, 128) comprising a shank (12) and first and second tool elements (46, 48; 46', 46''; 46'''), which tool elements (46, 48; 46', 46'', 46''') are arranged or formed to be movable relative to each other and comprise respective electrodes (28; 58; 58'; 58''), the electrodes (28; 58; 58'; 58'') defining a minimum distance from each other, being opposed to each other and facing each other in an approximating position of the tool elements (46, 48; 46'; 46''; 46'''), wherein the first tool element (48) is arranged or formed at the distal end (22) of the shank (12), characterized in that the second tool element (46; 46'; 46''; 46''') is adapted to be brought from an operating position, in which it can be brought into the approximating position, into a removing position in which removing position a peripheral withdrawing line (154) defined by the electrode (58; 58'; 58'') of the second tool element (46; 46'; 46''; 46''') is shorter than a peripheral approximating line (152) defined by the electrode (58; 58'; 58'') in the approximating position.

2. The surgical instrument according to sentence 1, characterized in that a first peripheral tool line (156) defined by the second tool element (46; 46'; 46''; 46''') in the removing position is shorter than a second peripheral tool line (158) defined by the second tool element (46; 46'; 46''; 46''') in the operating position.

3. The surgical instrument according to sentence 1 or 2, characterized by a retaining means (82; 82') for securing the second tool element (46; 46'; 46''; 46''') in the operating position.

4. The surgical instrument according to sentence 3, characterized in that the retaining means (82; 82') and the second tool element (46; 46'; 46''; 46''') are arranged to be movable relative to each other.

5. The surgical instrument according to any one of the preceding sentences, characterized by a folding mechanism (200; 200'; 200''; 200''') for transferring the second tool element (46; 46'; 46''; 46''') from the operating position into the removing position and/or vice versa.

6. The surgical instrument according to sentence 5, characterized in that the folding mechanism (200; 200'; 200''; 200''') comprises a first force transmission element (40) for transmitting an actuating force to the retaining means (82; 82') for transferring the latter from the operating position into the removing position and/or vice versa.

7. The surgical instrument according to sentence 6, characterized in that the retaining means (82; 82' and a second force transmission element (38) for transmitting an actuating force to the second tool element (46; 46'; 46''; 46''') are arranged to be movable relative to each other for transferring the latter from the operating position into the approximating position and/or vice versa.

8. The surgical instrument according to sentence 7, characterized in that the second force transmission element (38) and the retaining means (82; 82') are configured to be movable and/or twistable and/or screwable relative to each other.

9. The surgical instrument according to any one of the sentences 6 to 8, characterized in that the retaining means (82; 82') and/or the first and/or second force transmission element (38; 40) are arranged to be movable relative to the shank (12).

10. The surgical instrument according to any one of the sentences 5 to 9, characterized by an actuating mechanism (96) coupled to the folding mechanism (200; 200'; 200''; 200''') and/or the second force transmission element (38) and/or the retaining means (82; 82') for actuating the folding mechanism (200; 200'; 200''; 200''') and/or for moving the second force transmission element (38) and/or the retaining means (82; 82') relative to the shank (12).

11. The surgical instrument according to any one of the preceding sentences, characterized in that the second tool element (46; 46'; 46''; 46''') comprises at least two tool element members (74; 74'; 74''; 74''') coupled to the second electrode (58; 58') or supporting a part thereof.

12. The surgical instrument according to sentence 11, characterized in that the at least two tool element members (74; 74'; 74''; 74''') are arranged or configured to be movable in the radial direction relative to a longitudinal axis (14) defined by the second tool element (46; 46'; 46''; 46''').

13. The surgical instrument according to sentence 11 or 12, characterized in that the at least two tool element members (74; 74'; 74''; 74''') are configured in the form of arms protruding at least partly in the radial direction.

14. The surgical instrument according to any one of the sentences 11 to 13, characterized in that the at least two tool element members (74; 74'; 74''; 74''') are arranged or fixed at the distal end of the second tool element (46; 46'; 46''; 46''') and the free ends (150; 150'; 150''; 150''') thereof point in the proximal or substantially proximal direction.

15. The surgical instrument according to any one of the sentences 11 to 14, characterized in that the at least two tool element members (74; 74'; 74''; 74''') are separated from each other by a straight or curved slit (72; 72'; 72''; 72''') extending in the radial or substantially radial direction.

16. The surgical instrument according to any one of the preceding sentences, characterized in that the electrode (58; 58'; 58'') of the second tool element (46) is configured as an electrode ring (60) having a variable circumference.

17. The surgical instrument according to sentence 16, characterized in that the electrode ring (60) is slotted in the radial direction.

18. The surgical instrument according to sentence 17, characterized in that the electrode ring (60) is hollow and defines an electrode ring passage (62) and in that in the electrode ring passage (62) an electrode ring balancing element (70) is movably held for connecting free ends (66, 68) of the slotted electrode ring (58).

19. The surgical instrument according to sentence 17, characterized in that the electrode ring (58') comprises plural electrode ring portions (164) separated from one another by slits (72'), each electrode ring portion being arranged or formed at a free end (150') of a tool element member (46').

20. The surgical instrument according to sentence 16, characterized in that the electrode ring (58") is self-contained and is made of elastic or expandable material.
21. The surgical instrument according to any one of the preceding sentences, characterized in that the second tool element (46; 46'; 46"; 46''') comprises a biasing means (80; 80'; 80") for holding the second tool element (46; 46'; 46"; 46''') biased against the retaining means (82; 82') in the operating position.
22. The surgical instrument according to sentence 21, characterized in that the biasing means (80; 80'; 80") includes at least one biasing member (78; 78'; 78").
23. The surgical instrument according to sentence 22, characterized in that the at least one biasing member (78; 78'; 78") is configured in the form of an at least partially spring-elastic element.
24. The surgical instrument according to sentence 22 or 23, characterized in that at least part of the at least two tool element members (78) comprises or forms a biasing member (76).
25. The surgical instrument according to any one of the sentences 3 to 24, characterized in that the retaining means (82) comprises a stop (85) acting to point in the radial direction away from a longitudinal axis (14) of the second tool element (46; 46'; 46"; 46'''), wherein the at least two tool element members (74; 74'; 74"; 74''') or the electrode (58; 58'; 58") of the second tool element (46; 46'; 46"; 46''') are directly or indirectly adjacent to said stop in the operating position.
26. The surgical instrument according to sentence 25, characterized in that the retaining means (82) includes an annular or substantially annular stop member (87) which surrounds the longitudinal axis (14) and forms or comprises the stop (85).
27. The surgical instrument according to sentence 26, characterized in that the stop member (87) is held to be movable in parallel to the longitudinal axis (14) and releases the at least two tool element members (74; 74'; 74"; 74''') or the electrode (58; 58'; 58") of the second tool element (46; 46'; 46"; 46''') upon transition from the operating position into the removing position.
28. The surgical instrument according to any one of the preceding sentences, characterized by a cutting element (88) for transecting body tissue.
29. The surgical instrument according to sentence 28, characterized in that the cutting element (88) is configured in the form of an annular blade surrounding the longitudinal axis (14).
30. The surgical instrument according to sentence 28 or 29, characterized in that the retaining means (82) comprises the cutting element (88).
31. The surgical instrument according to any one of the sentences 28 to 30, characterized in that a cutting edge (90) of the cutting element (88) points in the proximal direction.
32. The surgical instrument according to any one of the sentences 10 to 31, characterized in that the actuating mechanism (96) comprises at least one actuating member (98, 108) which is arranged or movably held at a proximal end or in a proximal end area of the instrument (10).

Figure 1:
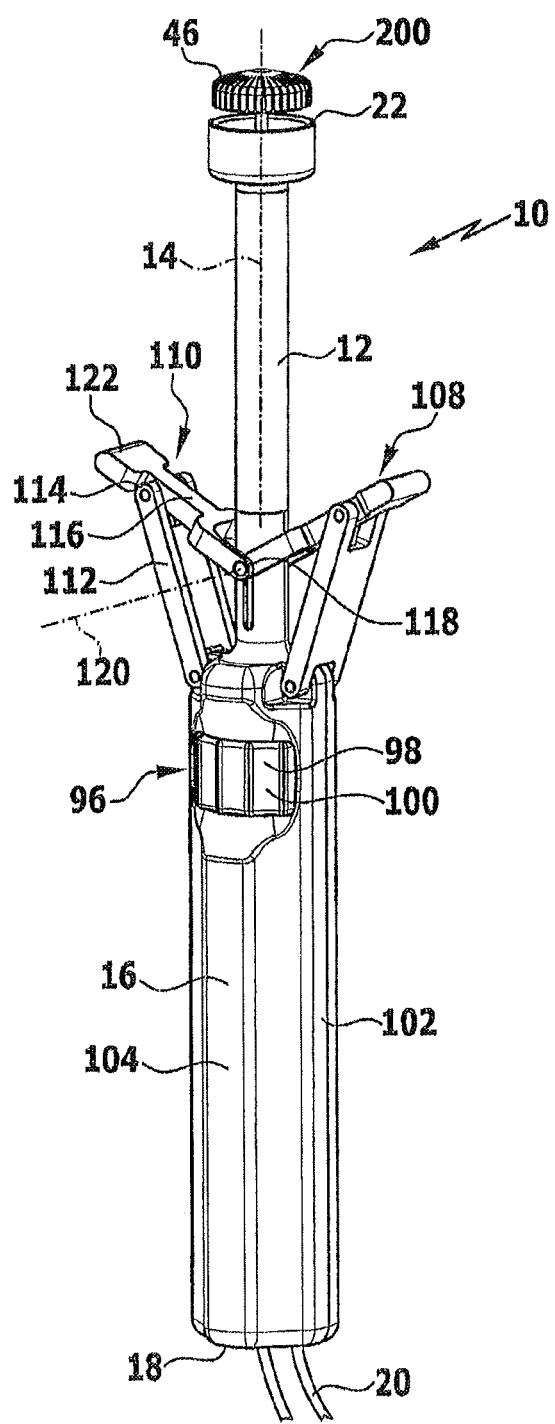
FIG. 1 shows a schematic perspective overall view of a surgical instrument for bonding body tissue.

FIG. 1 exemplifies a surgical instrument 10 for bonding body tissue. The surgical instrument 10 comprises an elongate shank 12 defining a longitudinal axis 14. A shank-like handle area 16 which extends approximately over half of a total length of the instrument 10 is connected to the proximal side of the shank 12. From a proximal end 18 of the handle area 16 a connecting line 20 protrudes for connecting the instrument 10 to a power supply not shown in the Figures, for example an HF generator.

The shank 12 extends towards a distal end 22 in the outer diameter substantially in single stage so that a short cylindrical receiving space 24 starting from the end 22 is formed which is open toward the distal direction. Starting from the end 22 a sleeve-like electrode 28 is inserted in the receiving space 24 adjacent to an inner wall 26 thereof, with the electrode defining an electrode surface 30 inclined in the direction of the longitudinal axis 14. The electrode 28 is connected to the connecting line 20 in an electrically conducting manner in a way not shown in detail.

Concentrically to and in the shank 12, an inner shank 32 extends approximately to the proximal end of the receiving space 24. It defines a passage 34. A cover 36 lines the receiving chamber 24 at the proximal side and leaves open merely the passage 34.

A rod-shaped first force transmission member 38 forms a guide in the inner shank 32. The rod-shaped first force transmission member 38 is surrounded by a second sleeve-like force transmission member 40 that is guided to be longitudinally displaceable. The force transmission members 38 and 40 are movable relative to each other in parallel to the longitudinal axis 14.

A first tool element 48 of the instrument 10 is formed by the end 22 with the electrode 28. A distal end 42 of the first force transmission member 38 engages positively in a recess 44 of a second tool element 46 opened in the proximal direction.

The second tool element 46 is configured as sort of a cover which has a slightly convexly curved end face 50 pointing in the distal direction having a blunt rounded tip 52. The end face 50 is transformed, spaced apart from the longitudinal axis 14, into an annular side wall 54 which, in an operating and approximating position of the instrument 10, is formed or aligned concentrically to the longitudinal axis 14. An end face 56 of the side wall 54 pointing in the proximal direction is concavely curved and serves for receiving and fastening an electrode 58 of the second tool element 46 configured in the form of an electrode ring 60. The electrode ring 60 is hollow and defines an electrode ring passage 62. The electrode ring 60 is designed to be not self-contained, but it is cut by a slit 64 so that ends 66 and 68 facing each other are slightly spaced apart from each other. In the electrode ring passage 62 an electrode ring balancing element 70 is inserted which interconnects the two ends 66 and 68 of the slotted electrode ring 60. Thus the altogether self-contained annular electrode 58 is formed which has two different outer diameters, i.e. a larger one which is defined by an outer diameter of the electrode ring 60 and a smaller outer diameter between the ends 66 and 68 which is defined by an outer diameter of the electrode ring balancing element 70.

The second tool element 46 is provided, starting out from the end wall 54, with a plurality of radial slits 72 that are evenly distributed over a circumference of the second tool element 46. In this way tool element members 74 held together at the tip 52 and extending therefrom in the radial direction and along the side wall 54 in the proximal direction are formed which have substantially the shape of an arm.

Due to the fact that the second tool element 46 is made of plastic material, the portions 76 forming part of the end face 50 constitute biasing members 78 in a biasing means 80 in total denoted with the reference numeral 80. The latter serves for the purpose of holding the second tool element 46 biased against a retaining means in total denoted with the reference numeral 82.

The retaining means 82 comprises a retaining disk 84 extending substantially transversely to the longitudinal axis 14 which is fixedly connected to the second force transmission member 40. The retaining disk 84 defines a maximum outer diameter 86 and is equipped with an annular sleeve-like cutting element 88 which concentrically surrounds the longitudinal axis 14 and has a cutting edge 90 pointing in the proximal direction which is self-contained. The cutting element 88 thus forms part of the retaining means 84. The retaining disk 84 and the cutting element 88 jointly form a stop member 87 which defines a stop for the tool element members 74 acting away from the longitudinal axis 14 in the radial direction. On the whole in this way a folding mechanism 200 is formed for virtually opening and closing the second tool element 46 in a way similar to an umbrella.

In an operating position of the instrument 10, as schematically shown in FIGS. 1 to 5, the tool element members 74 are slightly spread in the radial direction so that the retaining means 82 is completely inserted in the tool element 46 coming from the proximal direction. The cutting edge 90 is slightly reset vis-à-vis the electrode 58 in the distal direction so that the furthermost projecting part of the second tool element 46 is the electrode 58. Inner surfaces 92 of the tool element members 74, which thus constitute part of the side wall 54, due to the spreading are held to be biased against the retaining means 82, namely against the cutting element 88 and the retaining disk 84. Hence movement of free ends 94 of the tool element members 74 toward the longitudinal axis 14 is prevented by the retaining means 82.

The instrument 10 further comprises an actuating mechanism 96 including a first actuating element 98 in the form of a screw wheel 100 which concentrically surrounds the longitudinal axis 14 and is supported to be rotatable about the longitudinal axis 14 in a housing defined by the handle area 16. The screw wheel 100 is operatively connected to a portion 104 of the first force transmission member 38 thickened in the outer diameter which supports a screw thread 106. This permits moving the first force transmission member 38 in the distal or proximal direction by rotation of the screw wheel 100 about the longitudinal axis 14. A movement in the distal direction increases a distance between the electrodes 28 and 58; a movement of the first force transmission member in the proximal direction moves the electrode 58 toward the electrode 28.

The actuating mechanism 96 further comprises a second actuating member 108 in the form of a symmetric control arm arrangement 110. Two first control arms 112 are laterally offset to the longitudinal axis 14 and are pivoted about pivot axes at the housing 102 extending transversely to the longitudinal axis and in parallel to each other. Free ends 114 of the control arms 112 are pivoted in turn at a respective further control arm 116. Two free ends of the control arms 116 are pivotally coupled to each other as well as to the second force transmission member 40 about a pivot axis 120 vertically intersecting the longitudinal axis 14. Slightly offset against the other free ends 122, the ends 114 are pivoted with the control arm 116 about pivot axes extending in parallel to the pivot axis 120. Free ends 122 of the control arms 116 pointing away from the longitudinal axis form actuating members for actuating the second actuating element 108.

Figure 7:
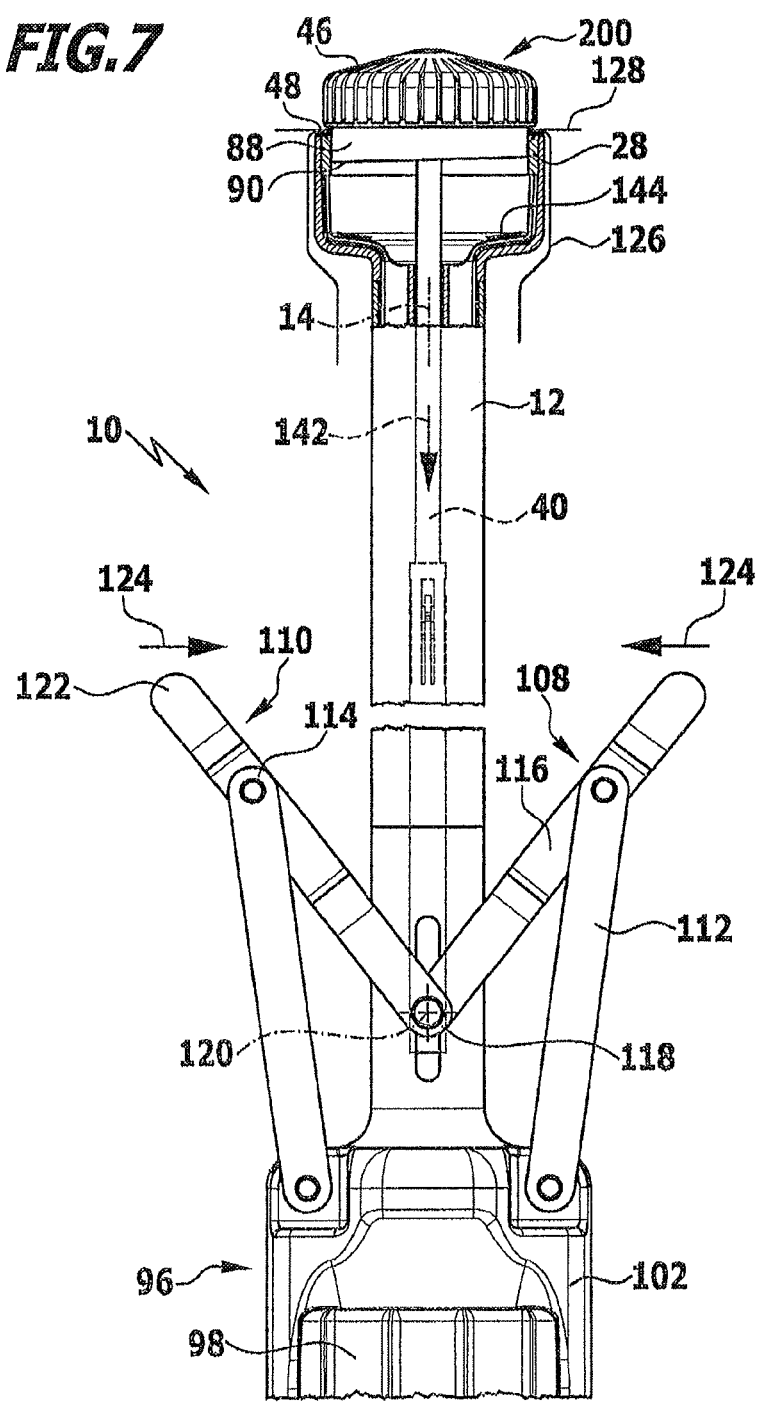
FIG. 7 is a view similar to the representation in FIG. 4 when transferring the instrument from the operating position into the removing position.
Figure 8:
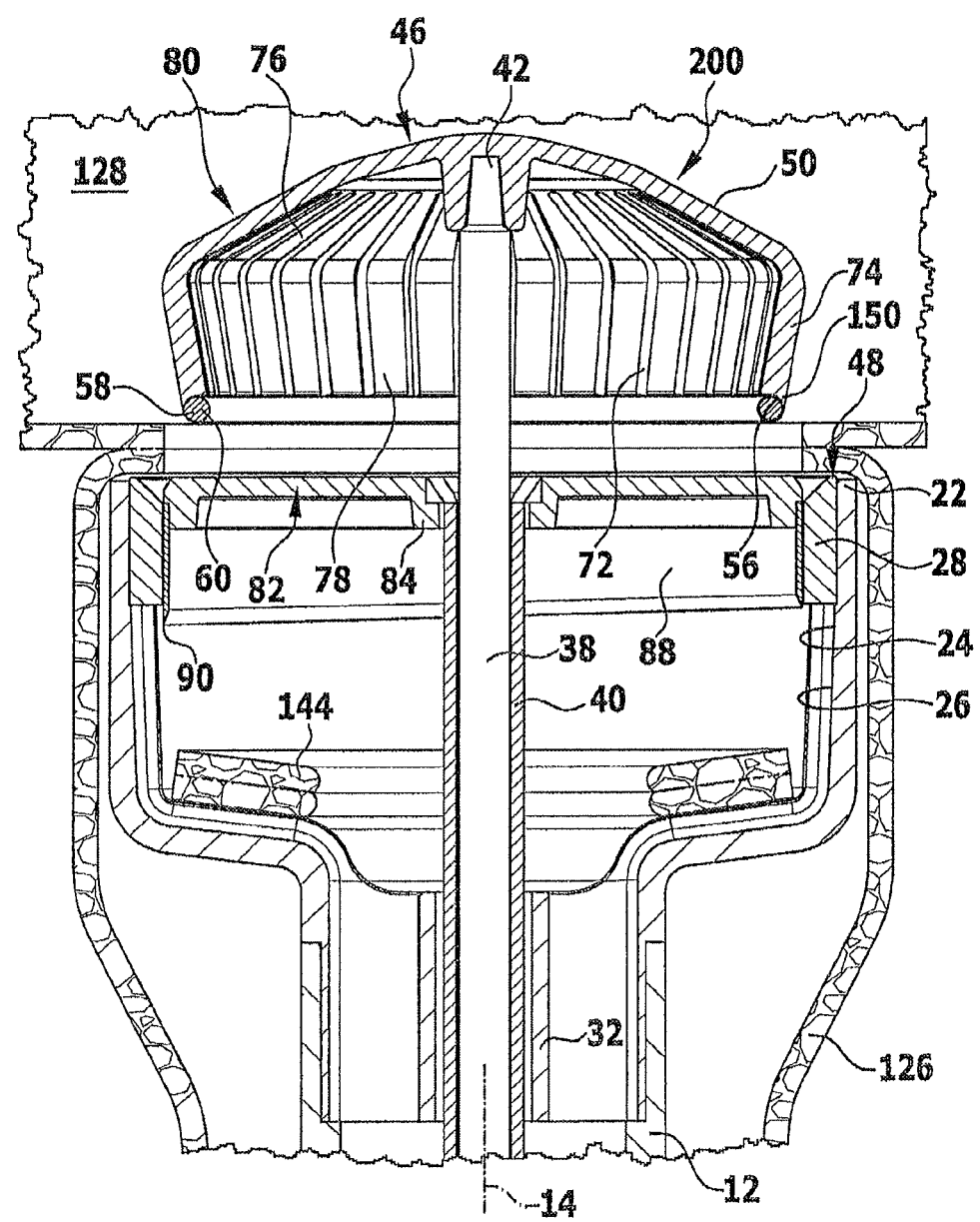
FIG. 8 is a view similar to the representation in FIG. 6 after transferring the second tool element from the operating position into the removing position.

When the ends 122 are pivoted toward each other in the direction of the arrows 124 as schematically shown in FIG. 7, the second force transmission member 40 is moved relative to the first force transmission member 38 in the proximal direction.

The functioning of the instrument 10 shall be illustrated hereinafter in combination with FIGS. 1 to 8, namely merely by way of example in connection with the production of an end-to-side anastomosis.

In order to laterally bond a first vessel 126 to a second vessel 128 the second vessel 128 is opened by a small incision 130. At the first vessel 126 slightly distant from the end 132 thereof an aperture is formed by a second incision 134. The distal end of the instrument 10 is inserted with the second tool element 46 ahead, which initially adopts the afore-mentioned operating position and is held to be biased in the same by the retaining means 82, into the first vessel 126 through the second incision 134 until the second tool element 46 projects from the end 132. The end 132 is laid inwardly over the electrode 28.

Figure 2:
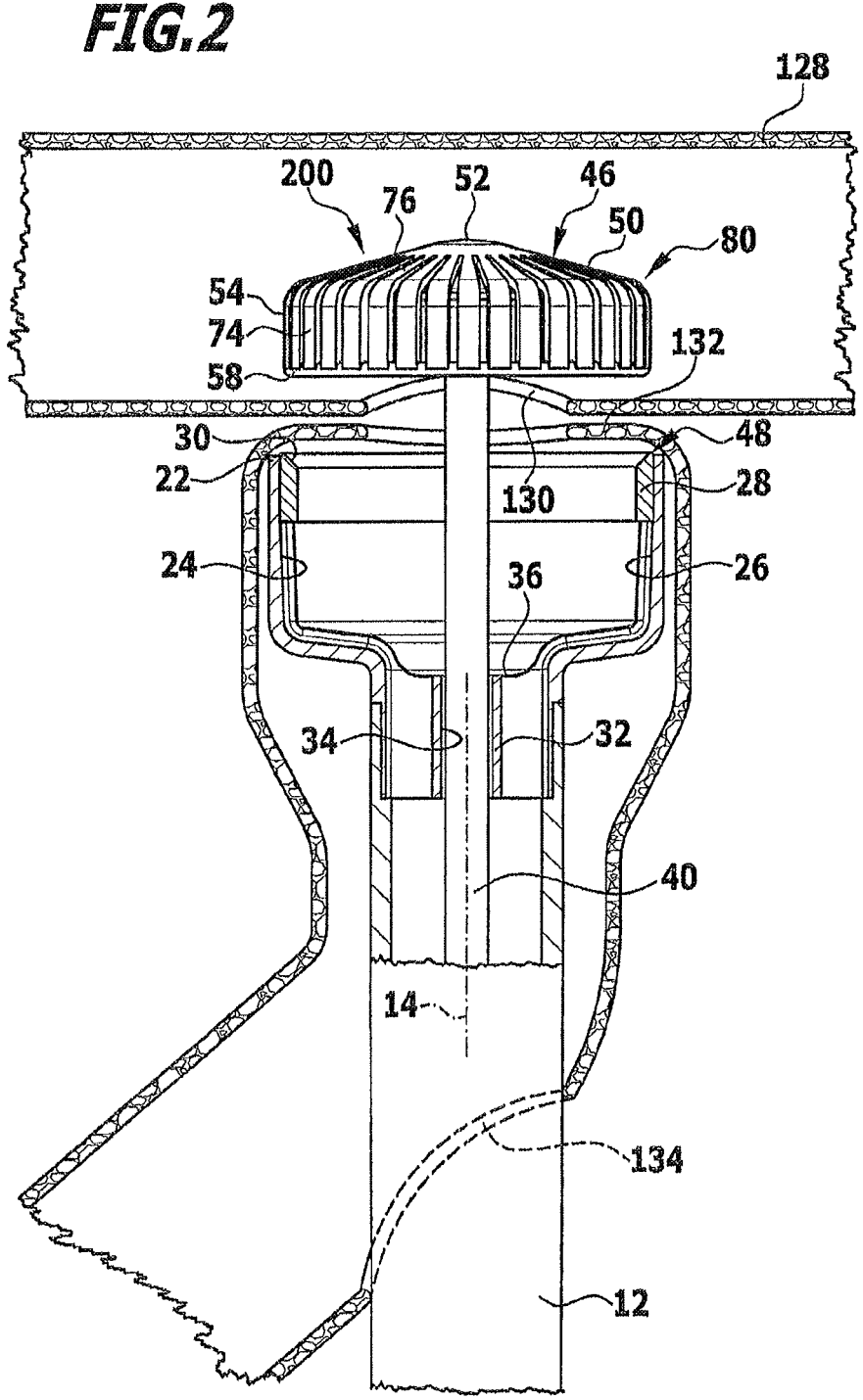
FIG. 2 shows a partly cut view of a distal end of the instrument illustrated in FIG. 1 when producing an end-to-side anastomosis.
Figure 3:
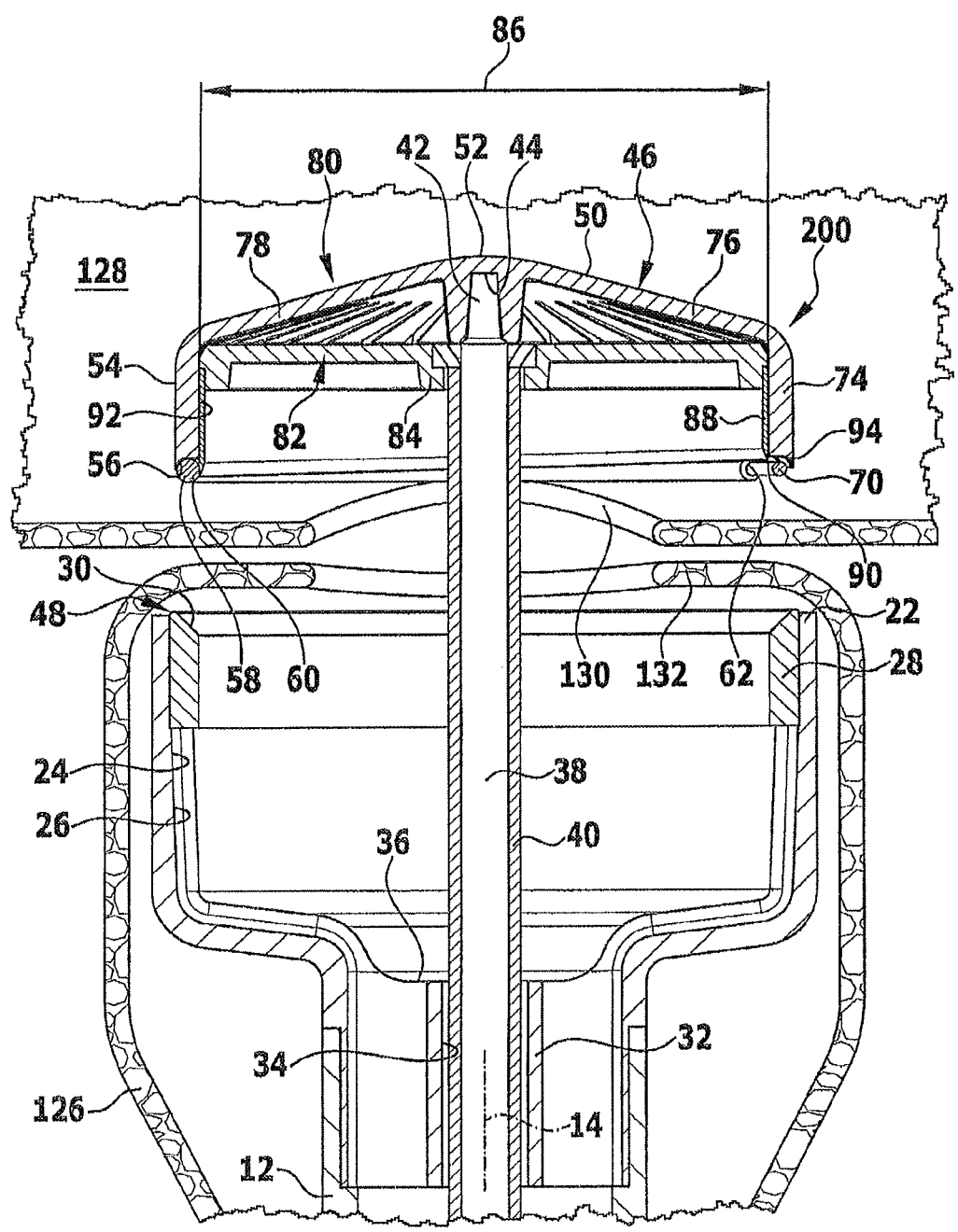
FIG. 3 shows an enlarged cutout view of the arrangement of FIG. 2.

In the next step the instrument 10 at which the first vessel 126 is held in the described manner is inserted into the second vessel 128 by the second tool element 46 through the first incision 130. This is schematically shown in FIG. 2. The vessels 126 and 128 are aligned so that the end 132 of the first vessel 126 covers the first incision 130 of the second vessel 128 as concentrically as possible. Thus two tissue layers are superimposed, as is schematically represented in FIG. 3.

Figure 4:
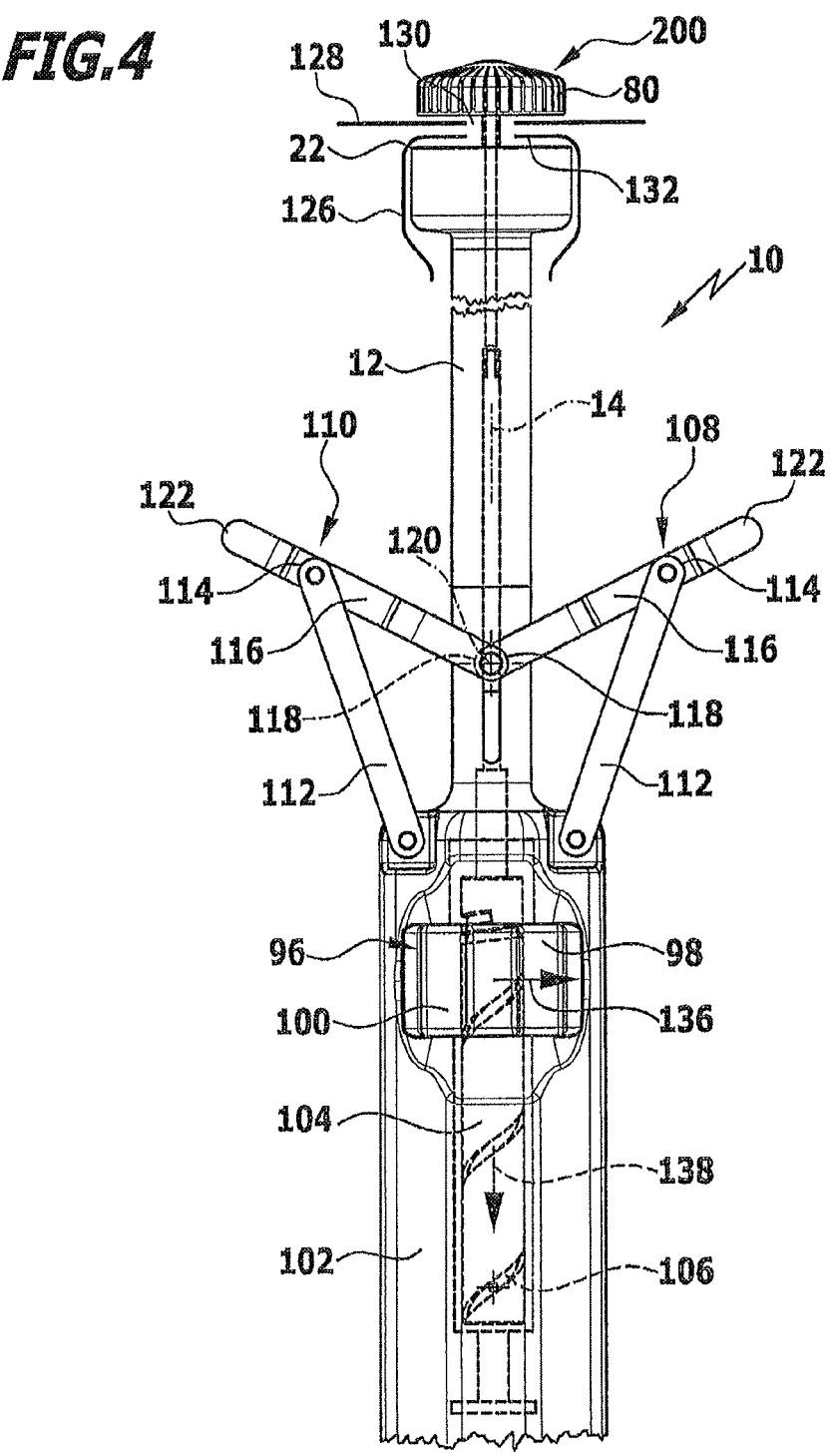
FIG. 4 shows a partly cut-through side view of the instrument before bonding of body tissue.

For bonding the superimposed tissue parts the screw wheel 110 is rotated in the direction of the arrow 136, as schematically represented in FIG. 4, so that the first force transmission member 38 is moved in the direction of the arrow 138 in the proximal direction.

Figure 5:
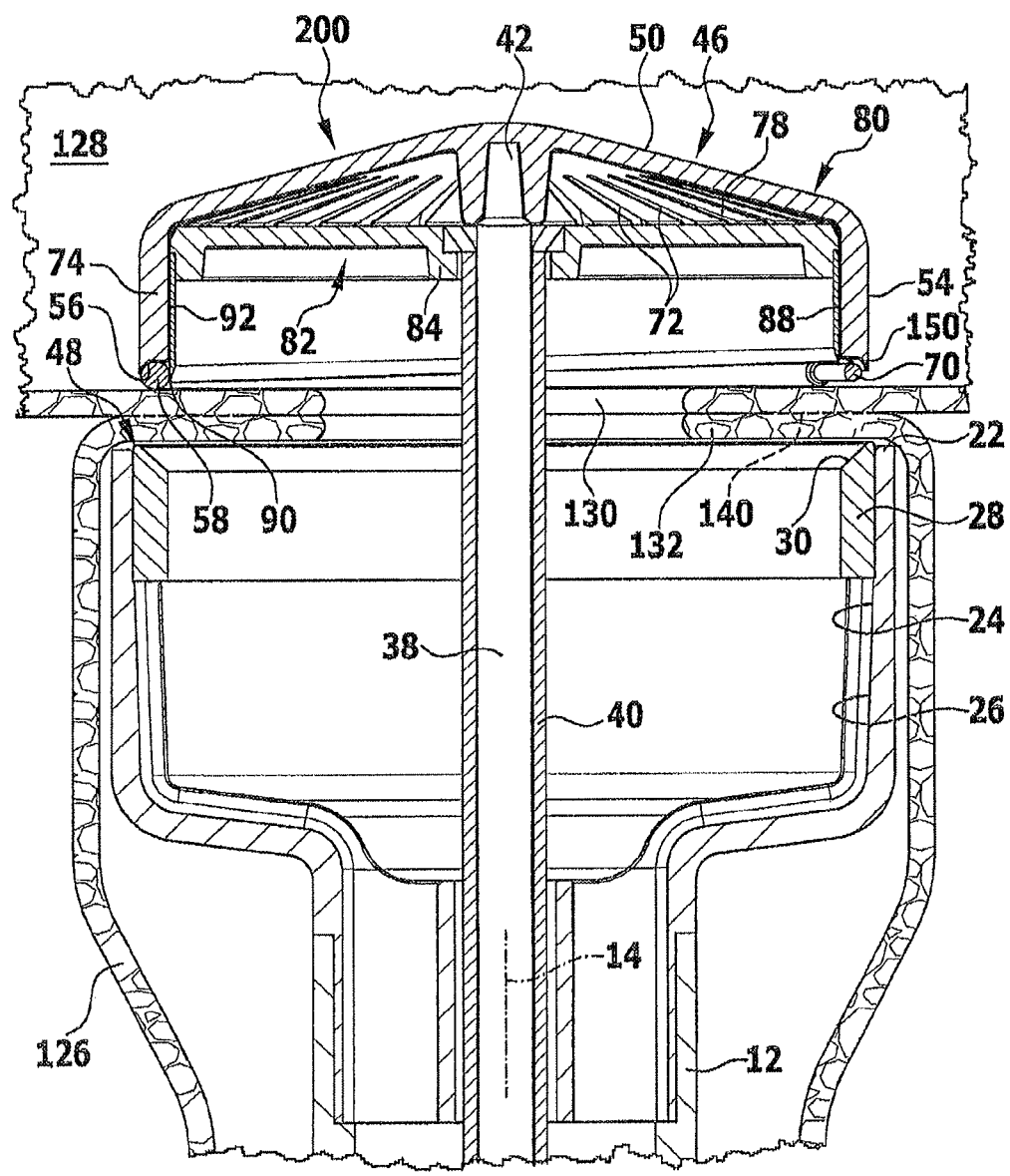
FIG. 5 is a view of the instrument similar to the representation in FIG. 3 during bonding of body tissue.
Figure 6:
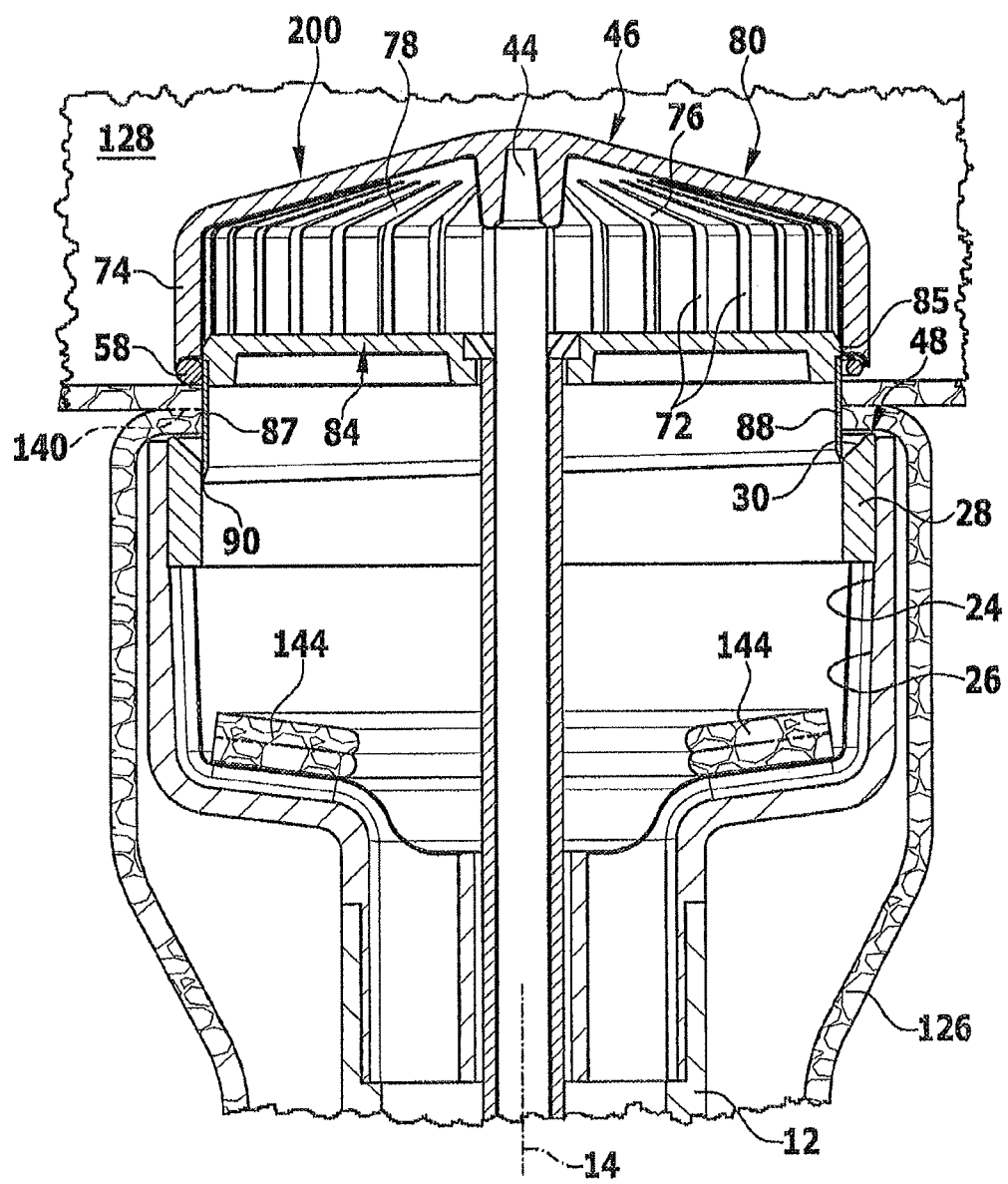
FIG. 6 is a view similar to the representation in FIG. 5 during resecting protruding body tissue in the area of the anastomosis.

As soon as the tool elements 46 and 48 adopt an approximating position in which they define a minimum distance from each other, as schematically shown in FIG. 5, the two tissue layers are adjacent to each other and are bonded by applying HF current to the electrodes 28 and 58. The bonding is performed by welding the vessels 126 and 128, as by the well-directed current flow via the electrodes 28 and 58 proteins contained in the vessels 126 and 128 are heated so far that they adhere to each other and produce a permanent and immediately loadable bonding along a self-contained annular anastomosis 140 between the electrodes 28 and 58.

As soon as the bonding between the vessels 126 and 128 has been completed in a defined manner, the instrument 10 can be withdrawn again. For this purpose, the instrument 10 is initially transferred from the approximating position into the removing position. This is performed by actuating the second actuating element 108, namely by swiveling the ends 122 in the direction of the arrows 124 toward each other. By moving the second force transmission member 40 in the proximal direction, i.e. in the direction of the arrow 142, as schematically represented in FIG. 7, also the retaining means 82 held at the second force transmission member 40 is moved in the proximal direction. As a result, also the cutting element 88 is moved in the proximal direction so that the cutting edge 90 can transect the bonded vessels 126 and 128 adjacent to the anastomosis 140 so that the tissue parts 144 protruding in the radial direction to the longitudinal axis 14 are resected and are collected in the receiving space 24.

During resection of the protruding tissue parts 144, the electrodes 28 and 58 maintain their mutual distance.

As soon as the retaining disk 84 has passed the electrode ring 60 in the proximal direction, the retaining means 82 releases the second tool element 46, especially free ends 150 of the tool element members 74 so that they can be moved by the biasing members 78 in the radial direction toward the longitudinal axis 14. Accordingly, a first distance 146 defined by the slit 72 in the operating position, as schematically shown in FIG. 9a, decreases to a smaller distance 148 in the removing position, as schematically represented in FIG. 9b. Since in this way also the free ends 150 of the tool element members 74 can come closer in the peripheral direction, a peripheral line of the electrode 58 decreases from a peripheral approximating line 152 in the operating or approximating position, as schematically plotted in FIG. 9a, to a peripheral withdrawing line in the removing position, as schematically shown in FIG. 9b. Thus the second tool element 46 is adapted to be brought from the operating position, in which it can be brought into the approximating position, to a removing position in which the peripheral withdrawing line 154 defined by the electrode 58 is shorter than the peripheral approximating line 152 defined by the electrode 58 in the approximating to position. The electrode 58 thus is variable also as to its periphery. Furthermore, also a first peripheral tool line 156 defined by the second tool element 46 in the removing position is shorter than a second peripheral tool line 158 defined by the second tool element 46 in the operating position, as schematically illustrated in FIGS. 9a and 9b.

As an alternative to the electrode ring 60 having an electrode ring balancing element 70, it would also be imaginable to design the electrode 58 not in a continuous manner but to design merely the remaining end face areas at the distal ends 150 of the tool element members 74 in an electrically conducting manner or to arrange electrode ring portions there. Then the electrode 58 would consist of a plurality of electrode ring portions separated from one another by the slits 72.

In FIGS. 10a to 12 another embodiment of a second tool element is schematically shown and in total is provided with the reference numeral 46'. The second tool element 46' substantially differs from the second tool element 46 by the structure of the electrode 58' as well as the biasing means 80'. The retaining means 82' is substantially identical to the retaining means 82. There are merely differences in the formation of the retaining disk 84' which comprises a plurality of ribs 160 orientated in the radial direction and facing the distal direction. Between two respective ribs 160 a seat 162 open in the distal direction is formed in which an electrode element 164 immerses in the operating or approximating position. Two electrode elements 164 are kept spaced apart from each other by a respective rib 160. The electrode elements 164 are substantially L-shaped and at their distal end include a projection 166 protruding in the radial direction away from the longitudinal axis 14, the projection forming a stop surface 168 pointing in the distal direction for the ends 150' of the tool element members 74'. The projection 166 further defines an electrode surface 170 which is outwardly inclined relative to the longitudinal axis 14'.

In the operating position a portion 172 of the tool element member 74' extends in parallel to the longitudinal axis 14' and in parallel to the cutting element 88. To the portion 172 a portion 174 directed transversely thereto and toward the longitudinal axis 14' is connected, which in turn is transformed into a portion 176 inclined by approximately 45° related to the longitudinal axis 14' and pointing in the direction of the tip 52'. A free end 178 defined by the portion 176 has a recess 180 opened toward the tip 52'. In the transition area between the portions 174 and 176 another recess 182 is formed which is opened pointing away from the longitudinal axis 14 in the radial direction. A first elastic ring 184 is Inserted into the recess 180 of the electrode elements 164 and is held in a non-positive and/or positive manner. A second elastic ring 186 expanded in the operating position is inserted in the recesses 182. It serves for exerting a tensile force on the electrode elements 164 in the operating position so as to hold the electrode elements 164 toward the longitudinal axis 14 biased against the retaining means 82'. Thus the ring 186 forms a biasing member 78'.

The electrode elements 164 are preferably formed of an electrically conducting material or are coated to be electrically conductive. The ring 184 preferably is equally made of electrically conductive material so that all electrode elements are interconnected to be electrically conducting by means of the electrode ring 184. Optionally the ring 186 can also be formed to be electrically conducting. However, it can also be made of an elastic plastic ring, for example.

A cutting plane defined by the cutting edge 90 can be inclined with respect to the longitudinal axis 14'. This may be provided not only in the retaining means 82' but also in the retaining means 82.

The functioning of the instrument 10 is identical irrespective of whether a second tool element 46 or a second tool element 46' is provided. When the instrument 10 is transferred into the removing position with the second tool element 46', as schematically shown in FIG. 11 in the operating position in which the second tool element 46' can also be brought into the approximating position, the retaining means 82' is analogously moved in the proximal direction so that the ring 186 can move the electrode elements 164 toward the longitudinal axis 14. In this way it is achieved that both a peripheral tool line defined by the second tool element 46' and a peripheral line defined by the electrode 58' are definitely longer in the approximating position than in the removing position. This is directly resulting from a reduction of the diameter of the second tool element 46' restricted by the free ends 150 of the tool element members 74', as schematically represented in FIGS. 11 and 12. Altogether in this way a folding mechanism 200' is formed for virtually opening and closing the second tool element 46' similarly to an umbrella.

Another embodiment of a second tool element is schematically illustrated in FIG. 13 and is in total provided with the reference numeral 46". It differs from the second tool element 46 substantially in that the free ends 150" of the tool element members 74" are triple bent or curved inwardly so that first a portion 190 extending in the radial direction is formed at the side wall 54", an adjacent portion 192 extending in parallel to the longitudinal axis 14 in the distal direction and a portion 194 inclined in the distal and radial directions which at the same time forms the free end 150". The portions 190, 192 and 194 thus virtually define a seat 196 for an electrode ring 60". The latter can be formed to be self-contained, for instance, and can completely or partly consist of nitinol. In this way it has an elasticity of up to approx. 8%. Thus at the same time it constitutes the biasing member 78" of a biasing means in total denoted with the reference numeral 80".

The second tool element 46" is schematically represented in the operating position in FIG. 13. In the operating position the portions 192 are adjacent to the retaining means 82 which is identical to the retaining means 82 described in connection with the FIGS. 1 to 9b. When the latter is displaced in the proximal direction in the afore-described manner by moving the 20 second force transmission member 40 in the proximal direction, the tool element members 74" are released and the electrode ring 60" can contract so as to reduce an electrode line defined by the electrode 58" upon transition from the approximating position into the removing position. On the whole, in this way a folding mechanism 200" is formed for virtually opening and closing the second tool element 46" similarly to an umbrella.

In FIG. 14 a further embodiment of a second tool element is schematically shown and is in total denoted with the reference numeral 46'". It is substantially different from the second tool element 46 by the fact that the slits 72'" separating the tool element members 74'" are not orientated away from the longitudinal axis 14 in the radial direction but extend away from the longitudinal axis 14 in a curved manner so that the spiral structure of the tool element members 74'" visible in FIG. 14 is formed. The second tool element 46'" can be equipped, especially similarly to the second tool element 46, with an electrode 58. Then it also permits, just as the second tool elements 46, 46' and 46", that a first peripheral tool line defined by the second tool element 46'" in the removing position is shorter than a 35 second peripheral tool line defined by the second tool element in the operating position. Moreover, the second tool element 46'" equally permits to be brought from the operating position in which it can be brought into the approximating position into a removing position in which removing position a peripheral withdrawing line defined by the electrode 58 is shorter than a peripheral approximating line defined by the electrode 58 in the approximating position. On the whole, in this way a folding mechanism 200'" is formed for virtually opening and closing the second tool element 46'" similarly to an umbrella.

There is no need to describe and illustrate in more detail in which way each of the electrodes 28 and 58 is connected to be electrically conducting to the connecting line 20. Preferably they are electrically insulated from each other. It is easily possible to realize an electric supply to the electrode 58 especially via the force transmission members 38 and 40 and to provide appropriately conducting connections at the second tool elements 46, 46', 46" and 46'" as well as at the retaining means 82, 82' and 82" so as to be able to apply HF current to the electrodes 28 and 58 or 58', respectively.

What is claimed is:

1. A surgical instrument for bonding body tissue in a hollow organ, the surgical instrument comprising:
    an instrument shank or shaft having a distal end and a first tool element fixedly arranged on the distal end of the instrument shank or shaft;
    a second tool element positioned distally from the first tool element and supported by the instrument shank or shaft to be axially movable relative to the first tool element; and
    an annular sleeve-like cutting element being held in an axially moveable manner for cutting body tissue,
    the second tool element comprising a plurality of tool element members in the form of arms that are radially deflectable, the tool element members protruding at least in part in a radial direction and spaced apart from each other in a circumferential direction,
    the first tool element being equipped with at least one electrode having an annular shape,
    the second tool element being equipped with a plurality of electrode elements provided at proximal ends of each of the arms that respectively face the first tool element, the electrode elements being radially moveable by deflecting the arms, wherein the electrode elements are circumferentially distanced apart with clearances in between and thereby forming together an annular shape,
    the second tool element comprising a biasing member that exerts a biasing force to bias the tool element members in a radially inward direction and an axially moveable retaining disk arranged at a radial inner side of the tool element members,
    the cutting element comprising a cutting edge pointing in a proximal direction, the cutting element forming part of the retaining disk to jointly form a stop member which defines a stop for the tool element members,
    the stop member being operable in a first axial position to hold the tool element members against the biasing force of the biasing member in which the tool element members assume a maximum outer diameter,
    the stop member further operable in a second axial position to release the tool element members, allowing the tool element members to deflect radially inwardly by the biasing force of the biasing member and simultaneously the stop member cuts body tissue in the proximal direction.

2. The surgical instrument according to claim 1, wherein the retaining disk comprises a plurality of ribs extending in an axial direction, the plurality of ribs being distanced from each other in the circumferential direction.

3. The surgical instrument according to claim 2,
    wherein the plurality of ribs of the retaining disk comprise pairs of adjacent ribs, the retaining disk forming a seat between each pair of adjacent ribs, each seat being open in a distal direction and adapted to receive one of the plurality of electrode elements.

4. The surgical instrument according to claim 1, wherein the biasing member comprises a first elastic ring and a second elastic ring being distanced from the first elastic ring in an axial direction and being located at a radial outer side of the tool element members, the first elastic ring made of an electrically conductive material.

5. The surgical instrument according to claim 4, wherein the second elastic ring is made of an electrically conductive material.

6. The surgical instrument according to claim 1, wherein each of the electrode elements is substantially L-shaped and comprises a distal end that includes a projection defining an electrode surface.

* * * * *